(12) United States Patent
Ouali et al.

(10) Patent No.: US 9,034,384 B2
(45) Date of Patent: May 19, 2015

(54) POLYUREA MICROCAPSULES

(75) Inventors: Lahoussine Ouali, Geneva (CH); Marlène Jacquemond, Geneva (CH)

(73) Assignee: Firmenich SA, Geneva (CH)

( * ) Notice: Subject to any disclaimer, the term of this patent is extended or adjusted under 35 U.S.C. 154(b) by 159 days.

(21) Appl. No.: 13/980,232

(22) PCT Filed: Jan. 31, 2012

(86) PCT No.: PCT/EP2012/051567
§ 371 (c)(1),
(2), (4) Date: Jul. 17, 2013

(87) PCT Pub. No.: WO2012/107323
PCT Pub. Date: Aug. 16, 2012

(65) Prior Publication Data
US 2013/0295149 A1    Nov. 7, 2013

(30) Foreign Application Priority Data

Feb. 7, 2011    (EP) ..................................... 11153486

(51) Int. Cl.
| | |
|---|---|
| *A61K 8/11* | (2006.01) |
| *A61Q 13/00* | (2006.01) |
| *C11B 9/00* | (2006.01) |
| *B01J 13/16* | (2006.01) |
| *C11D 3/50* | (2006.01) |
| *A61K 8/84* | (2006.01) |
| *A61Q 15/00* | (2006.01) |

(52) U.S. Cl.
CPC . *C11B 9/00* (2013.01); *B01J 13/16* (2013.01); *C11D 3/505* (2013.01); *A61Q 13/00* (2013.01); *A61Q 15/00* (2013.01); *A61K 8/84* (2013.01); *A61K 8/11* (2013.01); *A61K 2800/412* (2013.01)

(58) Field of Classification Search
None
See application file for complete search history.

(56) References Cited

U.S. PATENT DOCUMENTS

| | | | |
|---|---|---|---|
| 5,304,448 | A | 4/1994 | Keoshkerian et al. |
| 2007/0202063 | A1 | 8/2007 | Dihora |

FOREIGN PATENT DOCUMENTS

| | | |
|---|---|---|
| EP | 1741775 B1 | 4/2009 |
| GB | 2432843 A | 6/2007 |
| GB | 2432850 A | 6/2007 |
| GB | 2432851 A | 6/2007 |
| GB | 2432852 A | 6/2007 |
| WO | WO2005/054422 A1 | 6/2005 |
| WO | WO2007/004166 A1 | 1/2007 |
| WO | WO2007/062733 A1 | 6/2007 |
| WO | WO2007/062833 A1 | 6/2007 |
| WO | WO2008/016684 A1 | 2/2008 |
| WO | WO2009/153695 A1 | 12/2009 |
| WO | WO2010/070602 A2 | 6/2010 |
| WO | WO 2010070602 A2 * | 6/2010 |

OTHER PUBLICATIONS

International Search Report and Written Opinion, application PCT/EP2012/051567, mailed Mar. 6, 2012.

* cited by examiner

*Primary Examiner* — Brian Gulledge
*Assistant Examiner* — Michael P Cohen
(74) *Attorney, Agent, or Firm* — Winston & Strawn LLP (57) ABSTRACT

The present invention relates to polyurea core-shell microcapsules having a polyurea shell comprising the reaction product of a polyisocyanate with guanazole and an amino acid. The invention concerns the capsules themselves as well as perfuming compositions and perfumed articles containing them and a process for producing them.

15 Claims, 4 Drawing Sheets

POLYUREA MICROCAPSULES

TECHNICAL FIELD

The present invention relates to polyurea core-shell microcapsules having a polyurea shell comprising the reaction product of a polyisocyanate with guanazole and an amino acid. The invention concerns the capsules themselves as well as perfuming compositions and perfumed articles containing them and a process for producing them.

BACKGROUND OF THE INVENTION AND PROBLEM TO BE SOLVED

One of the problems faced by the perfumery industry lies in the relatively rapid loss of the olfactive benefit provided by odoriferous compounds due to their volatility, particularly that of "top-notes". This problem is generally tackled using a delivery system, e.g. capsules containing a perfume, to release the fragrance in a controlled manner.

Polyurea capsules, formed by polymerisation between a polyisocyanate and a polyamine, are well known in the art. In particular, polyurea microcapsules wherein guanidine is reacted with a polyisocyanate are known.

However, it would be desirable to provide capsules bearing high anionic charge both at acidic and basic pH. Such capsules would be advantageous over the known neutral capsules, because the presence of such charges would improve the dispersion of the capsules and their compatibility with anionic consumer product bases such as for example shower gels, shampoos and detergents. The charges would also enable the capsules to interact with cationic polymers, which facilitate deposition of capsules on substrates to which they are applied, such as human skin, hair or fabric. Good deposition of the capsules is particularly useful because it is correlated with good olfactive performance of the capsules and the long-lastingness of such performance over time.

The present invention addresses these problems. It has surprisingly been discovered that polyurea microcapsules having a wall made of the reaction product of a polyisocyanate with an amino acid and guanazole were highly negatively charged and that the replacement of known polyamines by guanazole improved the capsules deposition and olfactive performance.

To the best of our knowledge, no prior art document discloses core-shell polyurea microcapsules having a wall comprising the reaction product of a polyisocyanate with guanazole and an amino acid.

Reaction of amino acids and polyisocyanates for the formation of capsules is described in U.S. Pat. No. 5,304,448. However, such document is completely silent with regard to reacting the polyisocyanate also with guanazole.

SUMMARY OF THE INVENTION

The present invention relates to polyurea core-shell microcapsules comprising:
 a polyurea shell comprising the reaction product of a polyisocyanate having at least two isocyanate groups with
  i. an amino acid; and
  ii. guanazole; and
 a core comprising a perfume.

In another embodiment, the invention relates to a liquid composition comprising polyurea microcapsules according to the present invention, together with a cationic polymer.

In a further embodiment, the invention relates to a perfuming composition or to a perfumed consumer article comprising the capsules of the invention.

In a still further embodiment, the invention relates to a process for the preparation of the microcapsules of the invention comprising:
 a) dissolving at least one polyisocyanate having at least two isocyanate groups in a perfume;
 b) adding an aqueous solution of an amino acid to the mixture obtained in step a) to react with the polyisocyanate; and
 c) adding an aqueous solution of guanazole to the mixture obtained in step b), to react with the reaction product of the polyisocyanate with the amino acid, so as to form a polyurea wall.

DETAILED DESCRIPTION OF THE DRAWINGS

DETAILED DESCRIPTION OF THE INVENTION

One object of the present invention is polyurea core-shell microcapsules comprising:
 a polyurea shell comprising the reaction product of a polyisocyanate having at least two isocyanate groups with
  i. an amino acid; and
  ii. guanazole; and
 a core comprising a perfume.

The polyisocyanate can be any type of polyisocyanate comprising at least two isocyanate groups. Preferably it contains at least three isocyanate groups. Following these numbers of functional groups, an optimal reticulation or network of the capsules wall is achieved, providing thus microcapsules exhibiting a prolonged slow release of fragrances, as well as an improved stability in the consumer product. Low volatility polyisocyanate molecules are preferred because of their low toxicity.

Preferably, the polyisocyanate is an aliphatic polyisocyanate, an aromatic polyisocyanate or a mixture thereof. When the polyisocyanate is in the form of a mixture of aliphatic and aromatic polyisocyanates, the at least one aliphatic polyisocyanate and the at least one aromatic polyisocyanate are preferably used in a respective molar ratio comprised between 80:20 and 10:90, more preferably between 75:25 and 20:80, even more preferably between 60:40 and 20:80 and most preferably between 60:40 and 30:70. Such molar ratio is defined as the relative ratio of the number of moles of isocyanate groups provided by the at least one aliphatic polyisocyanate and the number of moles of the isocyanate groups provided by the at least one aromatic polyisocyanate.

The term "aromatic polyisocyanate" is meant here as encompassing any polyisocyanate comprising an aromatic moiety. Preferably, it comprises a phenyl, a toluoyl, a xylyl, a naphthyl or a diphenyl moiety, more preferably a toluoyl or a xylyl moiety. Preferred aromatic polyisocyanates are biurets and polyisocyanurates, more preferably comprising one of the above-cited specific aromatic moieties. More preferably, the aromatic polyisocyanate is a polyisocyanurate of toluene diisocyanate (commercially available from Bayer under the tradename Desmodur® RC), a trimethylol propane-adduct of toluene diisocyanate (commercially available from Bayer under the tradename Desmodur® L75), a trimethylol propane-adduct of xylylene diisocyanate (commercially available from Mitsui Chemicals under the tradename Takenate® D-110N). In a most preferred embodiment, the aromatic polyisocyanate is a trimethylol propane-adduct of xylylene diisocyanate.

Figure 1:
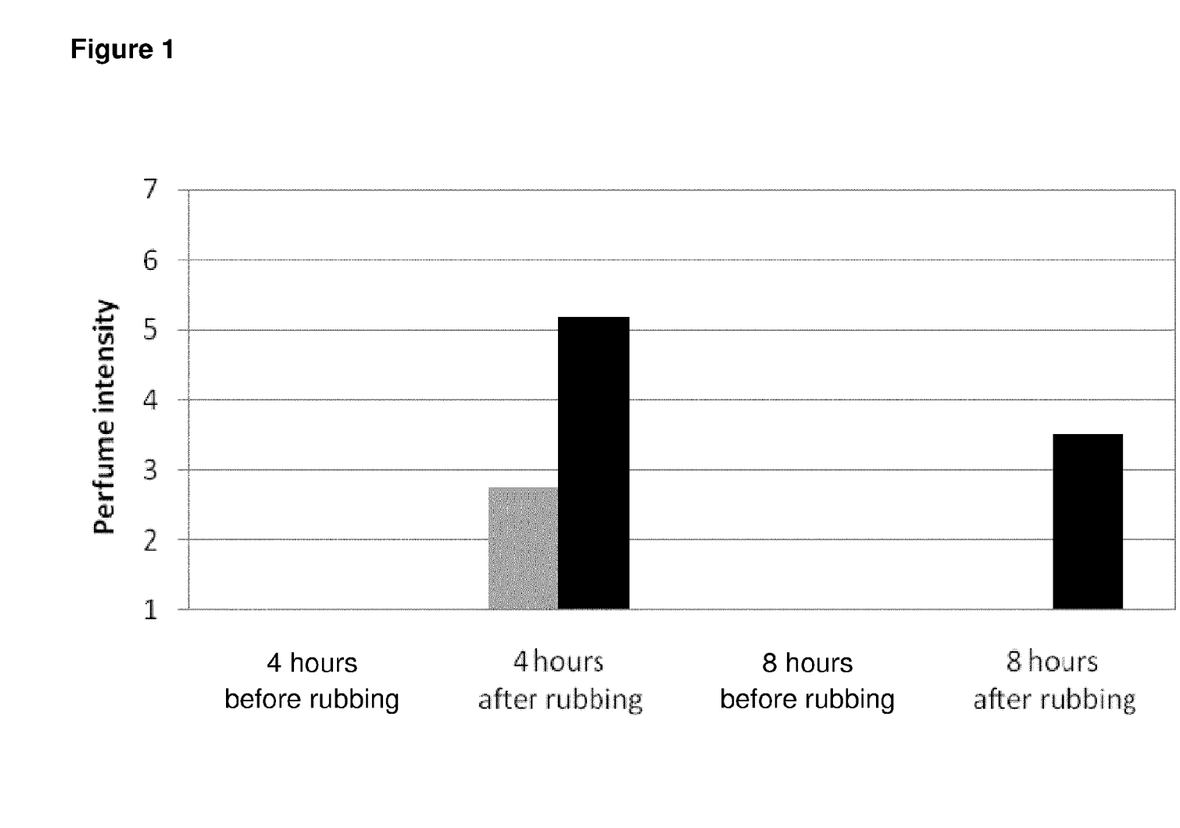
FIG. 1 represents the results of the olfactive evaluation of the capsules of Examples 1 (Capsules A, invention) and 8 (Capsules H, comparative) in body wash application. The perceived perfume intensity of Capsules A is represented in black and that of Capsules H is represented in grey.

The term "aliphatic polyisocyanate" is defined as a polyisocyanate which does not comprise any aromatic moiety. Preferred aliphatic polyisocyanates are a trimer of hexamethylene diisocyanate, a trimer of isophorone diisocyanate, a trimethylol propane-adduct of hexamethylene diisocyanate (available from Mitsui Chemicals) or a biuret of hexamethylene diisocyanate (commercially available from Bayer under the tradename Desmodur® N100), among which a biuret of hexamethylene diisocyanate is even more preferred. The chemical structure of this preferred aliphatic polyisocyanate is represented in FIG. 1.

Examples of preferred specific mixtures of at least one aliphatic polyisocyanate and of at least one aromatic polyisocyanate are a mixture of a biuret of hexamethylene diisocyanate with a trimethylol propane-adduct of xylylene diisocyanate, a mixture of a biuret of hexamethylene diisocyanate with a polyisocyanurate of toluene diisocyanate and a mixture of a biuret of hexamethylene diisocyanate with a trimethylol propane-adduct of toluene diisocyanate. Most preferably, it is a mixture of a biuret of hexamethylene diisocyanate with a trimethylol propane-adduct of xylylene diisocyanate.

Preferably the polyisocyanate is added in an amount comprised between 1 and 40%, preferably between 2 and 20% by weight, relative to the total weight of perfume and polyisocyanate (oily phase).

Guanazole is intended here as the polyamine compound 3,5-diamino-1H-1,2,4-triazole, which is commercially available from diverse suppliers. This specific polyamine surprisingly provides improved deposition on substrates such as human skin, hair or wool, compared to polyamines known for the preparation of polyurea microcapsules such as guanidine, as shown in the Examples.

The presence of the amino acid in the polyurea microcapsules wall is advantageous in that it is negatively charged over a wide range of pH, ranging from acidic to basic pH. It is also easily included in the polyurea wall due to its good reactivity with polyisocyanates. Any amino acid can be used in the capsules according to any embodiment of the present invention. Natural or artificial amino acids can be used, among which natural amino acids are preferred. Lysine and glycine are particularly preferred. Lysine, preferably L-lysine is the most preferred amino acid for the purpose of the present invention.

The total amount of guanazole and amino acid is preferably adjusted so that the molar ratio of isocyanate groups relative to amine groups is comprised between 1 and 0.2. More preferably, the molar ratio of amine groups provided by guanazole, relative to amine groups provided by the amino acid is comprised between 0.5 and 2.

The polyurea wall of the microcapsules is the result of the interfacial polymerisation between the polyisocyanate and guanazole and the amino acid, as defined in any embodiment of the invention.

The specific composition of the present polyurea wall is key in obtaining microcapsules that are at the fine balance between release and retention so as to achieve satisfactory slow and constant release of fragrances over time, once the capsules are to a surface such as for example human skin or hair, while showing the desired stability in the product base (e.g. counteracts efficiently the extraction of the perfume by the surfactants of the consumer product).

The perfume comprised in the core of the microcapsules according to any embodiment of the present invention can be a perfuming ingredient alone or a mixture of ingredients in the form of a perfuming composition. Specific examples of such perfuming ingredients may be found in the current literature, for example in Perfume and Flavour Chemicals, 1969 (and later editions), by S. Arctander, Montclair N.J. (USA), as well as in the vast patent and other literature related to the perfume industry. They are well known to the person skilled in the art of perfumery, that is, of imparting a pleasant odour to a consumer product or composition.

The perfuming ingredients may be dissolved in a solvent of current use in the perfume industry. The solvent is preferably not an alcohol. Examples of such solvents are diethyl phthalate, isopropyl myristate, Abalyn® (rosin resins, available from Eastman), benzyl benzoate, ethyl citrate, limonene or other terpenes, or isoparaffins. Preferably, the solvent is very hydrophobic and highly sterically hindered, like for example Abalyn®. Preferably the perfume comprises less than 30% of solvent. More preferably the perfume comprises less than 20% and even more preferably less than 10% of solvent, all these percentages being defined by weight relative to the total weight of the perfume. Most preferably, the perfume is essentially free of solvent.

According to an embodiment of the invention, the perfume used in the process of the invention contains at most 10% of its own weight of primary alcohols, at most 15% of its own weight of secondary alcohols and at most 20% of its own weight of tertiary alcohols. Preferably, the perfume used in the process of the invention does not contain any primary alcohols and contains at most 15% of secondary and tertiary alcohols.

According to another preferred embodiment of the invention, the perfume is present in an amount of between 10 and 60%, preferably between 25 and 60%, these percentages being defined by weight relative to the total weight of the capsules.

The microcapsules according to any embodiment of the present invention can optionally comprise an anionic stabilizer or surfactant. Examples of such anionic surfactants include acylglycinate salts (such as that sold by Ajinomoto under the trade name Amilite®), sericin or anionic polyvinyl alcohol (such as that sold by Kuraray under the trade name Mowiol® KL-506). Cellulose polymers, for example sodium carboxymethylcellulose polymers, such as those sold by Hercules under the trade name Ambergum®, can also be used as possible surfactants in the capsules of the present invention.

The microcapsules of the present invention can comprise other optional ingredients such as antioxidants and antimicrobial or antifoaming agents.

The microcapsules of any embodiment of the invention preferably have a mean diameter comprised between 1 and 50

μm and preferably comprised between 5 and 30 μm. In the present context, "mean diameter" refers to the arithmetic mean.

The microcapsules of the present invention bear anionic charges over a broad range of pH ranging from acidic to basic pH and are preferably characterised by a Zeta potential comprised between −50 and −120 mV, preferably between −60 and −110 mV. For the purpose of the present invention, the zeta potential is defined as measured using Zetasizer Nano ZS (Malvern Instruments).

The capsules of the present invention can be provided in a dry form or in the form of a liquid composition or slurry comprising a suspension of the capsules in water, such as for example that obtained directly in the end of the preparation process described below. In such liquid composition, the amount of water is preferably comprised between 45 and 60% by weight, relative to the total weight of the composition.

A liquid composition comprising the capsules as defined in any of the above embodiments and further comprising a cationic polymer is another aspect of the present invention. Any of such polymers known for use in diverse home and personal care consumer products can be used. Preferred cationic polymers preferably comprise a hydrophobic moiety. The main examples of cationic polymers known to be substantive to hair and skin include quaternized synthetics, cellulose derivatives, quaternized guars, lanolin, animal and vegetable proteins, and aminosilicones. Examples of such cationic polymers include cationic cellulosic guar hydroxypropyl triammonium polymers (such as for example those sold by Rhodia under the trade name Jaguar®), similarly modified hydroxypropyl trimethyl ammonium chloride ether of hydroxyethyl celluloses such as the Polyquaternium 10 UCare Polymers JR, LR and LK supplied by Amerchol Corporation, acrylamido-propyl trimonium chloride/acrylamide copolymers (such as the ones sold by BASF under the trade name Salcare®), polyquaternium polymers, among which copolymers of polyvinyl pyrrolidone and polyvinylimidazole (such as those sold by BASF under the trade name Luviquat® Ultra Care), cationic acrylates (such as the Merquat® copolymers of dimethyl diallyl ammonium chloride with acrylamide sold by NALCO). Other quaternized materials such as quaternized lanolin, chitosan, collagen and wheat proteins are also valid cationics. Finally, aminosilicones such as Quaternium 80 (ABILQUATS 3270, 3272 sold by Goldschmidt) may also be used. The capsules of the present invention are able to interact in a very efficient way with such cationic polymers, so that the deposition of the capsules on a surface to which they are applied, especially on skin, hair or fabric, is further improved.

In another embodiment, the invention provides a process for the preparation of polyurea microcapsules comprising:
a) dissolving at least one polyisocyanate having at least two isocyanate groups in a perfume;
b) adding an aqueous solution of an amino acid to the mixture obtained in step a) to react with the polyisocyanate; and
c) adding an aqueous solution of guanazole to the mixture obtained in step b) to react with the reaction product of the polyisocyanate with the amino acid, so as to form a polyurea wall.

Preferably, the process of the invention further comprises adding an anionic surfactant or stabilizer. Such surfactant or stabilizer, if used, is added to the mixture of step a) prior to the addition of the amino acid.

An emulsion or dispersion can be prepared by high shear mixing and adjusted to the desired droplet size. Droplet size may be checked with light scattering measurements or microscopy. For the purpose of the present invention, a dispersion is characterized by the stabilization of the oil droplets by a colloidal stabilizer, in contrast to an emulsion, wherein the oil droplets are stabilized by emulsifiers.

No specific action is required to induce the polymerisation between the polyisocyanates, guanazole and the amino acid in the dispersion. The reaction starts immediately after adding these reactants. Preferably the reaction is maintained for 2 to 15 hours, more preferably for 3 to 10 hours.

The polyurea wall components, the perfume and the stabilizer or emulsifier are as defined above in any embodiment of the invention, in relation to the description of the capsules themselves.

The microcapsules of the invention can be advantageously used for the controlled release of the encapsulated perfume. It is therefore particularly appreciated to include these microcapsules as perfuming ingredients in a perfuming composition or in a perfumed consumer product. This result is highly surprising since said consumer products may contain high amounts (typically more than 10% of their own weight) of specific types of surfactant/tensioactive/solvents and which are known to significantly diminish the stability and the performance of capsules. In other words, the use of the invention's microcapsules in the consumer products provides unexpected advantages over the same use of other similar prior art capsules.

As shown in the examples below, the anionic polyurea microcapsules obtained by the process of the invention provide improved deposition of the perfume on the treated surface. They also have good stability in a chemically aggressive environment and thus a good retention of the perfume. The anionic polyurea microcapsules are also well dispersed in the consumer product bases, so that no phase separation is induced upon addition of the capsules to the base and during a sufficient storage period. The microcapsules of the invention provide a controlled release of the encapsulated perfume, said perfume being slowly released from the microcapsules, thus considerably improving the perfume long-lastingness and intensity.

A perfumed consumer product or a perfuming composition comprising the microcapsules of the invention or the liquid aqueous composition of the invention is therefore also an object of the present invention. In particular the consumer product may be in the form of a home- or personal-care product. Preferably, it is in the form of a liquid shampoo, hair conditioner, shower gel, antiperspirant, deodorant, detergent, all-purpose cleaner or fabric softener, in the form of a soap or in the form of a powder or tablet detergent. As detergents we include here products such as detergent compositions or cleaning products for washing up or for cleaning various surfaces, for example intended for the treatment of textiles, dishes or hard surfaces (floors, tiles, stone-floors, etc), preferably for the treatment of textile. Preferred consumer products according to the present invention are shower gels, hair care products such as shampoos and hair conditioners, antiperspirants and deodorants, among which shower gels and hair care products are mostly preferred.

The reaction mixture obtained in the process of the invention may be used as such to perfume the consumer products. Alternatively, the microcapsules obtained in the process of the invention may be isolated from the reaction mixture before being incorporated into a consumer product. Similarly, the reaction mixture comprising the microcapsules of the invention may be sprayed onto a dry, powdered product, such as a washing powder or powdered detergent or the microcapsules may be dried and added to these products in solid form.

In order to further improve the deposition of the capsules on the substrate to which they are applied, the capsules of the present invention can advantageously be incorporated in the consumer product of the present invention together with a cationic polymer. Such cationic polymer preferably comprises a hydrophobic moiety. The main examples of cationic polymers known to be substantive to hair and skin include quaternized synthetics, cellulose derivatives, quaternized guars, lanolin, animal and vegetable proteins, and aminosilicones. Examples of such cationic polymers include cationic cellulosic guar hydroxypropyl triammonium polymers (such as for example those sold by Rhodia under the trade name Jaguar®), similarly modified hydroxypropyl trimethyl ammonium chloride ether of hydroxyethyl celluloses such as the Polyquaternium 10 UCare Polymers JR, LR and LK supplied by Amerchol Corporation, acrylamido-propyl trimonium chloride/acrylamide copolymers (such as the ones sold by BASF under the trade name Salcare®), polyquaternium polymers, among which copolymers of polyvinyl pyrrolidone and polyvinylimidazole (such as those sold by BASF under the trade name Luviquat® Ultra Care), cationic acrylates (such as the Merquat® copolymers of dimethyl diallyl ammonium chloride with acrylamide sold by NALCO). Other quaternized materials such as quaternized lanolin, chitosan, collagen and wheat proteins are also valid cationics. Finally, aminosilicones such as Quaternium 80 (ABILQUATS 3270, 3272 sold by Goldschmidt) may also be used. The capsules of the present invention are able to interact in a very efficient way with such cationic polymers, so that the deposition of the capsules on a surface to which they are applied, especially on skin, hair or fabric, is further improved.

Preferably, the consumer product of the present invention comprises a sufficient amount of capsules to achieve a perfume content in the final product comprised between 0.01 and 1%, preferably between 0.1 to 0.2% by weight, relative to the total weight of the consumer product. When the capsules are added to the consumer product in the form of a slurry as obtained directly from the process described below, this corresponds to an amount of such slurry comprised between 0.02 and 3%, more preferably between 0.15 and 2% by weight relative to the total weight of the consumer product. Of course the above concentrations may be adapted according to the olfactive effect desired in each product.

Formulations of consumer product bases in which the microcapsules of the invention can be incorporated can be found in the abundant literature relative to such products. These formulations do not warrant a detailed description here, which would in any case not be exhaustive. The person skilled in the art of formulating such consumer products is perfectly able to select the suitable components on the basis of his general knowledge and of the available literature. In particular, examples of such formulations can be found in the patents and patent applications relative to such products, for example in WO 2008/016684 (pages 10 to 14), in US 2007/0202063 (paragraphs [0044] to [0099]), in WO 2007/062833 (pages 26 to 44), in WO 2007/062733 (pages 22 to 40), in WO 2005/054422 (pages 4 to 9), in EP 1741775, in GB 2432843, in GB 2432850, in GB 2432851 or in GB 2432852.

EXAMPLES

The following examples are further illustrative of the present invention embodiments, and further demonstrate the advantages of the invention devices relative to prior art teachings.

Example 1

Preparation of Polyurea Microcapsules According to the Invention

A perfume was prepared by admixing 20% of each of the following ingredients: hexyl salicylate, Romascone® (methyl 2,2-dimethyl-6-methylene-1-cyclohexanecarboxylate, origin: Firmenich SA, Geneva, Switzerland), Lilial® (3-(4-tert-butylphenyl)-2-methylpropanal, origin: Givaudan SA, Vernier, Switzerland), Vertenex® (4-tert-butyl-1-cyclohexyl acetate, origin: International Flavors and Fragrances, USA) and Verdox® (2-tert-butyl-1-cyclohexyl acetate, origin: International Flavors and Fragrances, USA).

Microcapsules according to the invention (Capsules A) were prepared having the following ingredients in the amount indicated.

TABLE 1

Composition of Capsules A

| Ingredient | Amount [%] w/w |
| --- | --- |
| Perfume[1] | 30.0 |
| Desmodur ® N100[2] | 6.8 |
| Amino acid[3] | 1.3 |
| Guanazole | 2.0 |
| Amilite ® GCS11[4] | 0.3 |
| Water | 59.6 |
| Total | 100.0 |

[1] Perfume prepared as described above
[2] Biuret of hexamethylene diisocyanate, origin: Bayer
[3] L-lysine
[4] Acylglycinate salt, origin: Ajinomoto A 28.6% w/w solution of guanazole in water was prepared. A 20.6% w/w solution of the amino acid in water was prepared and the pH was adjusted to 11 using a 30% solution of NaOH. A 0.6% w/w solution of Amilite® GCS11 in water was prepared and the pH was adjusted to 10, using a 30% NaOH solution.

The Desmodur® N100 was diluted into the perfume. The obtained solution was then poured into the Amilite® GCS11 solution prepared above and dispersed using an Ultra Turax® apparatus during 3 minutes at 13500 rpm, to form an emulsion. The pH of the emulsion was adjusted to 11 using a 30% NaOH solution.

The obtained emulsion was then poured into a three necked reactor. A mechanical stirrer with disc anchor was connected to the outlet and stirring of the emulsion at 300 rpm was started. The amino acid solution was then added dropwise in 30 minutes using a Stepdos pump. The pH was controlled. The guanazole solution was then added dropwise in 30 minutes using the same equipment. The pH was also controlled. The system was then slowly heated under mechanical stirring to 55° C. over 30 minutes and then from 55° C. to 70° C. over 30 minutes. The system was kept under mechanical stirring for 3 hours at 70° C. Finally the capsules dispersion was cooled down to room temperature.

The zeta potential of the obtained capsules was measured using a Zetasizer Nano ZS (Malvern Instruments). A value of −68.7±4.1 mV was obtained.

Example 2

Preparation of Polyurea Microcapsules According to the Invention

Microcapsules according to the invention (Capsules B) were prepared having the following ingredients in the amount indicated.

TABLE 2

| Composition of Capsules B | |
| --- | --- |
| Ingredient | Amount [%] w/w |
| Perfume[1] | 30.0 |
| Desmodur ® N100[2] | 6.8 |
| Amino acid[3] | 2.0 |
| Guanazole | 1.6 |
| Amilite ® GCS11[4] | 0.3 |
| Water | 59.3 |
| Total | 100.0 |

[1] Perfume prepared in Example 1
[2] Biuret of hexamethylene diisocyanate, origin: Bayer
[3] L-lysine
[4] Acylglycinate salt, origin: Ajinomoto The microcapsules were prepared as described in Example 1, except that the amino acid solution in water was prepared at a concentration of 28.6% w/w and the guanazole solution was prepared at a concentration of 16.7% w/w.

The zeta potential of the obtained capsules was measured using a Zetasizer Nano ZS (Malvern Instruments). A value of −69.5±1.4 mV was obtained.

Example 3

Preparation of Polyurea Microcapsules According to the Invention

Microcapsules according to the invention (Capsules C) were prepared having the following ingredients in the amount indicated.

TABLE 3

| Composition of Capsules C | |
| --- | --- |
| Ingredient | Amount [%] w/w |
| Perfume[1] | 30.0 |
| Desmodur ® N100[2] | 6.8 |
| Amino acid[3] | 1.3 |
| Guanazole | 2.0 |
| Amilite ® GCS11[4] | 0.3 |
| Water | 59.6 |
| Total | 100.0 |

[1] Perfume prepared in Example 1
[2] Biuret of hexamethylene diisocyanate, origin: Bayer
[3] Glycine
[4] Acylglycinate salt, origin: Ajinomoto The microcapsules were prepared as described in Example 1.

The zeta potential of the obtained capsules was measured using a Zetasizer Nano ZS (Malvern Instruments). A value of −102±6.2 mV was obtained.

Example 4

Preparation of Polyurea Microcapsules According to the Invention

Microcapsules according to the invention (Capsules D) were prepared having the following ingredients in the amount indicated.

TABLE 4

| Composition of Capsules D | |
| --- | --- |
| Ingredient | Amount [%] w/w |
| Perfume[1] | 30.0 |
| Desmodur ® N100[2] | 6.8 |
| Amino acid[3] | 2.0 |
| Guanazole | 1.6 |
| Amilite ® GCS11[4] | 0.3 |
| Water | 59.3 |
| Total | 100.0 |

[1] Perfume prepared in Example 1
[2] Biuret of hexamethylene diisocyanate, origin: Bayer
[3] Glycine
[4] Acylglycinate salt, origin: Ajinomoto The microcapsules were prepared as described in Example 2.

The zeta potential of the obtained capsules was measured using a Zetasizer Nano ZS (Malvern Instruments). A value of −98.7±6.4 mV was obtained.

Example 5

Preparation of Polyurea Microcapsules According to the Invention

Microcapsules according to the invention (Capsules E) were prepared having the following ingredients in the amount indicated.

TABLE 5

| Composition of Capsules E | |
| --- | --- |
| Ingredient | Amount [%] w/w |
| Perfume[1] | 30.0 |
| Desmodur ® N100[2] | 6.7 |
| Amino acid[3] | 1.5 |
| Guanazole | 1.8 |
| Water | 60.0 |
| Total | 100.0 |

[1] Perfume prepared in Example 1
[2] Biuret of hexamethylene diisocyanate, origin: Bayer
[3] L-Lysine A 18.6% w/w solution of guanazole in water was prepared. A 78.5% w/w solution of the amino acid in water was prepared and the pH was adjusted to 11 using a 30% solution of NaOH.

The Desmodur® N100 was diluted in the perfume.

The Desmodur® N100 was poured to the solution of amino acid. This mixture was stirred during 3 minutes. The obtained solution was then poured into the mixture of Desmodur® N100 and perfume and dispersed using an Ultra Turax® apparatus during 4 minutes at 24000 rpm, to form an emulsion.

The obtained emulsion was then poured into a three necked reactor. A mechanical stirrer with disc anchor was connected to the outlet and stirring of the emulsion at 550 rpm was started. The guanazole solution was then added dropwise during 2 hours using the same equipment. The pH was also controlled. The system was then slowly heated under mechanical stirring to 55° C. over 30 minutes and then from 55° C. to 70° C. over 30 minutes. The system was kept under mechanical stirring for 3 hours at 70° C. Finally the capsules dispersion was cooled down to room temperature.

The zeta potential of the obtained capsules was measured using a Zetasizer Nano ZS (Malvern Instruments). A value of −42.5±2.2 mV was obtained.

Example 6

Preparation of Polyurea Microcapsules According to the Invention

Microcapsules according to the invention (Capsules F) were prepared having the following ingredients in the amount indicated.

TABLE 6

| Composition of Capsules F | |
| --- | --- |
| Ingredient | Amount [%] w/w |
| Perfume[1] | 30.0 |
| Desmodur ® N100[2] | 6.0 |
| Takenate ® D110N[5] | 1.4 |
| Amino acid[3] | 2.0 |
| Guanazole | 1.6 |
| Amilite ® GCS11[4] | 0.3 |
| NaOH 30% | 1.1 |
| Water | 57.6 |
| Total | 100.0 |

[1] Perfume prepared in Example 1
[2] Biuret of hexamethylene diisocyanate, origin: Bayer
[3] Lysine
[4] Acylglycinate salt, origin: Ajinomoto
[5] Aromatic isocyanate adduct prepolymer based on Xylylene Diisocynate dissolved in ethyl acetate, origin: Mitsui Chemicals Inc.

The microcapsules were prepared as described in Example 1, except that the amino acid solution in water was prepared at a concentration of 38.4% w/w and the guanazole solution was prepared at a concentration of 19.4% w/w. The mixture of Takenate® D 110N and Desmodur® N100 was diluted in the perfume.

The zeta potential of the obtained capsules was measured using a Zetasizer Nano ZS (Malvern Instruments). A value of −72.8±2.1 mV was obtained.

Example 7

Preparation of Polyurea Microcapsules According to the Invention

Microcapsules according to the invention (Capsules G) were prepared having the following ingredients in the amount indicated.

TABLE 7

| Composition of Capsules G | |
| --- | --- |
| Ingredient | Amount [%] w/w |
| Perfume[1] | 30.0 |
| Desmodur ® N100[2] | 6.8 |
| Amino acid[3] | 2.0 |
| Guanazole | 1.6 |
| PVOH KL506[4] | 1.3 |
| Water | 58.3 |
| Total | 100.0 |

[1] Perfume prepared in Example 1
[2] Biuret of hexamethylene diisocyanate, origin: Bayer
[3] Lysine
[4] Modified polyvinyl alcohol with carboxylic group, origin: Kuraray The microcapsules were prepared as described in Example 1, except that the amino acid solution in water was prepared at a concentration of 38.4% w/w and the guanazole solution was prepared at a concentration of 25% w/w. The Amilite® GCS11 was replaced by the PVOH KL506.

The zeta potential of the obtained capsules was measured using a Zetasizer Nano ZS (Malvern Instruments). A value of −38.2±2.0 mV was obtained.

Example 8

Preparation of Polyurea Microcapsules (Comparative)

Microcapsules (Capsules H) were prepared having the following ingredients in the amount indicated.

TABLE 8

| Composition of Capsules H | |
| --- | --- |
| Ingredient | Amount [%] w/w |
| Perfume[1] | 30.0 |
| Desmodur ® N100[2] | 6.8 |
| Amino acid[3] | 1.3 |
| Guanidine carbonate | 1.8 |
| Amilite ® GCS11[4] | 0.3 |
| Water | 59.8 |
| Total | 100.0 |

[1] Perfume prepared in Example 1
[2] Biuret of hexamethylene diisocyanate, origin: Bayer
[3] L-lysine
[4] Acylglycinate salt, origin: Ajinomoto The microcapsules were prepared as described in Example 1, except that guanidine carbonate was used instead of guanazole, as indicated in the table above. The solution of guanidine carbonate was prepared at a concentration of 26.5% w/w and the amino acid solution was prepared at a concentration of 20.6% w/w.

The zeta potential of the obtained capsules was measured using a Zetasizer Nano ZS (Malvern Instruments). A value of −55±0.9 mV was obtained.

Example 9

Preparation of Polyurea Microcapsules (Comparative)

Microcapsules (Capsules I) were prepared having the following ingredients in the amount indicated.

TABLE 9

| Composition of Capsules I | |
| --- | --- |
| Ingredient | Amount [%] w/w |
| Perfume[1] | 30.0 |
| Desmodur ® N100[2] | 6.8 |
| Amino acid[3] | 2.0 |
| Guanidine carbonate | 1.5 |
| Amilite ® GCS11[4] | 0.3 |
| Water | 59.4 |
| Total | 100.0 |

[1] Perfume prepared in Example 1
[2] Biuret of hexamethylene diisocyanate, origin: Bayer
[3] L-lysine
[4] Acylglycinate salt, origin: Ajinomoto The microcapsules were prepared as described in Example 8, except that the amino acid solution in water was prepared at a concentration of 28.6% w/w and the guanidine carbonate solution was prepared at a concentration of 21.9% w/w.

The zeta potential of the obtained capsules was measured using a Zetasizer Nano ZS (Malvern Instruments). A value of −74.8±0.9 mV was obtained.

Example 10

Preparation of Polyurea Microcapsules (Comparative)

Microcapsules (Capsules J) were prepared having the following ingredients in the amount indicated.

TABLE 10

Composition of Capsules J

| Ingredient | Amount [%] w/w |
| --- | --- |
| Perfume[1] | 30.0 |
| Desmodur ® N100[2] | 6.8 |
| Amino acid[3] | 1.3 |
| Guanidine carbonate | 2.0 |
| Amilite ® GCS11[4] | 0.3 |
| Water | 59.6 |
| Total | 100.0 |

[1]Perfume prepared in Example 1
[2]Biuret of hexamethylene diisocyanate, origin: Bayer
[3]Glycine
[4]Acylglycinate salt, origin: Ajinomoto The microcapsules were prepared as described in Example 8.

The zeta potential of the obtained capsules was measured using a Zetasizer Nano ZS (Malvern Instruments). A value of −62.3±8.5 mV was obtained.

Example 11

Preparation of Polyurea Microcapsules (Comparative)

Microcapsules (Capsules K) were prepared having the following ingredients in the amount indicated.

TABLE 11

Composition of Capsules K

| Ingredient | Amount [%] w/w |
| --- | --- |
| Perfume[1] | 30.0 |
| Desmodur ® N100[2] | 6.8 |
| Amino acid[3] | 2.0 |
| Guanidine carbonate | 1.4 |
| Amilite ® GCS11[4] | 0.3 |
| Water | 59.5 |
| Total | 100.0 |

[1]Perfume prepared in Example 1
[2]Biuret of hexamethylene diisocyanate, origin: Bayer
[3]Glycine
[4]Acylglycinate salt, origin: Ajinomoto The microcapsules were prepared as described in Example 9.

The zeta potential of the obtained capsules was measured using a Zetasizer Nano ZS (Malvern Instruments). A value of −46±4.5 mV was obtained.

Example 12

Body Wash Product Comprising the Capsules of the Invention and Olfactive Evaluation Thereof A body wash formulation was prepared having the following ingredients in the amount indicated.

TABLE 12

Composition of the body wash formulation

| Ingredient | Amount [%] w/w |
| --- | --- |
| Carbopol ® Aqua CC polymer[1] | 8.0 |
| Citric acid (40% solution in water) | 0.5 |
| Zetesol AO 328 U[2] | 25.0 |
| Tego ® Betain F 50[3] | 4.0 |
| Glydant Plus Liquid[4] | 0.1 |
| Sodium Chloride (20% solution in water) | 4.0 |
| Water | 58.4 |

[1]Polyacrylate-1 crosspolymer, origin: Noveon
[2]Sodium $C_{12}$-$C_{15}$ pareth sulfate, origin: Zschimmer & Schwarz
[3]Cocamidopropyl betaine, origin: Goldschmidt AG
[4]DMDM hydantoin and iodoproynyl butylcarbamate, origin: Lonza Capsules A (according to the invention) as obtained in Example 1 and Capsules H (comparative) as obtained in Example 8 were respectively dispersed in the body wash formulation prepared above (Body Wash A and H), so as to achieve a perfume content of 0.2% by weight, relative to the total weight of the body wash formulation (corresponding to 0.67% by weight of the capsules as obtained in Examples 1 and 8, respectively). An amount of 0.5% by weight of an acrylamido-propyl trimonium chloride/acrylamide copolymer (Salcare®, origin: BASF) was also added to the body wash base.

Body Washes A and H were applied to wool swatches intended to mimic human skin. The wool swatches were wetted during 30 s under running water at 38° C. Body Washes A and H were then respectively applied in an amount of 0.5 g with a micropipette and lather was then created during 10 seconds by rubbing a finger on the whole surface. The swatches were then rinsed during 20 seconds under running water at 38° C. and finally allowed to dry on a hotplate at 32° C.

The perfume intensity was then evaluated on a blind basis by an expert panel consisting of 4 trained panelists who were asked to rate the perceived perfume intensity on the wool swatches on a scale ranging from 1 to 7, wherein 1 means no odor and 7 means very strong odor, respectively 4 and 8 hours after application of Body Washes A and H. The perfume intensity was evaluated both before and after rubbing the wool swatch with the hand.

The results are summarized in FIG. 1. It is clear from these results that the perfume intensity was much more intense with Body Wash A (with the capsules of the invention), than with Body Wash H (comparative example). Even if low intensity is observed before rubbing with both samples, the capsules according to the invention proved to provide a much more intense perfume intensity after rubbing, both after 4 and after 8 hours. After 8 hours in particular, the perfume is still clearly perceived from the swatches washed with Body Wash A, whereas it is not anymore perceived from the swatches washed with Body Wash H. This difference in perfume intensity provides evidence of a better deposition of the capsules comprising guanazole, compared to those comprising guanidine carbonate.

Example 13

Olfactive Evaluation of the Microcapsules of the Invention

Capsules B (according to the invention) as obtained in Example 2 and Capsules I (comparative) as obtained in Example 9 were respectively dispersed in the body wash formulation prepared in Example 9 (Body Wash B and I) so as to achieve a perfume content of 0.2% by weight, relative to the total weight of the body wash formulation (corresponding to 0.67% by weight of the capsules as obtained in Examples 1 and 9, respectively). An amount of 0.5% by weight of an acrylamido-propyl trimonium chloride/acrylamide copolymer (Salcare®, origin: BASF) was also added to the body wash base.

Body Washes B and I were applied to wool swatches intended to mimic human skin, as described in Example 12. The perfume intensity was then evaluated on a blind basis by an expert panel consisting of 4 trained panelists who were asked to rate the perceived perfume intensity on the wool swatches on a scale ranging from 1 to 7, wherein 1 means no odor and 7 means very strong odor, 7 hours and 45 minutes after application of Body Washes B and I. The perfume intensity was evaluated both before and after rubbing the wool swatch with the hand.

Figure 2:
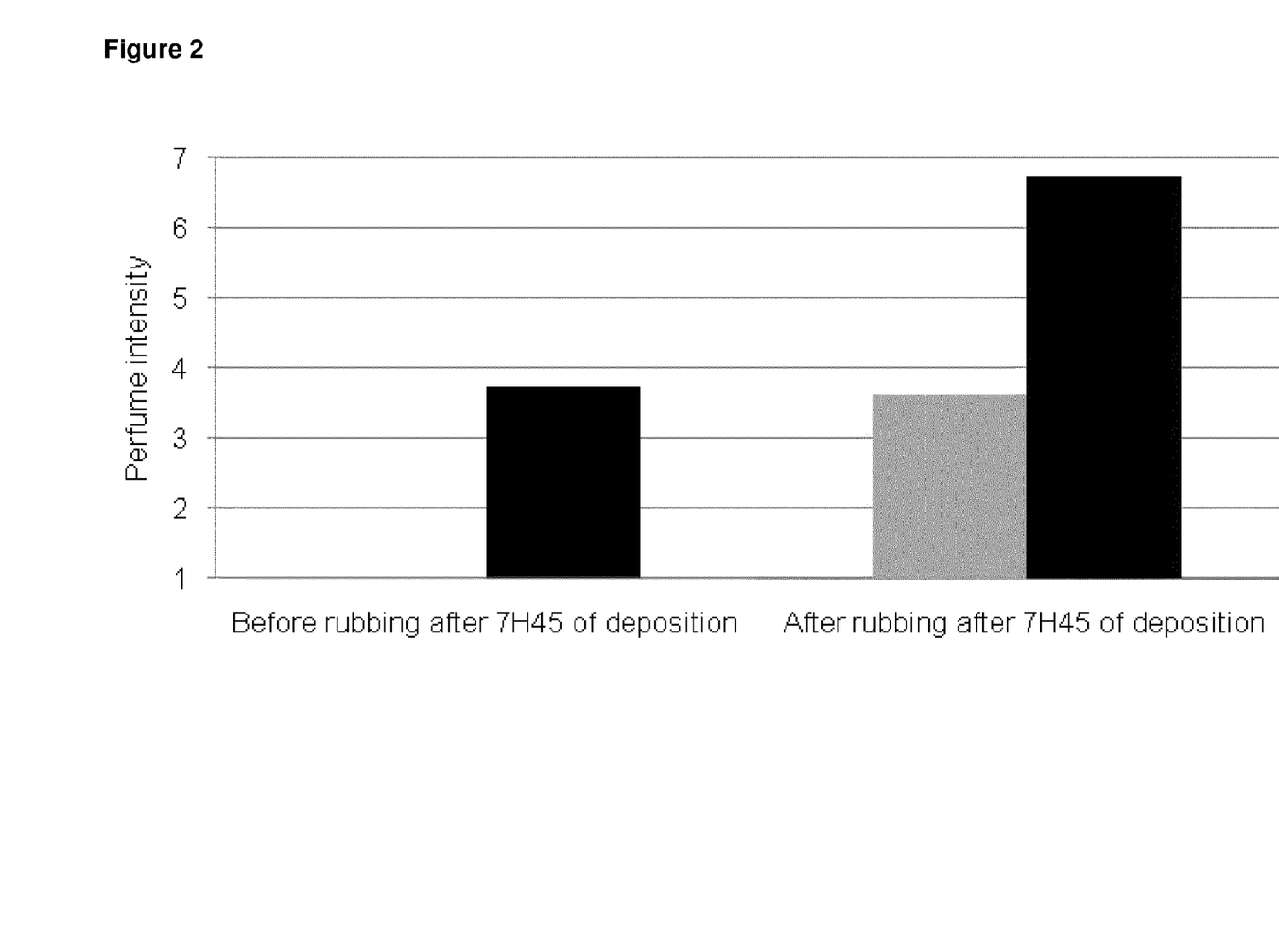
FIG. 2 represents the results of the olfactive evaluation of the capsules of Examples 2 (Capsules B, invention) and 9 (Capsules I, comparative) in body wash application. The perceived perfume intensity of Capsules B is represented in black and that of Capsules I is represented in grey.

The results are summarized in FIG. 2. It is clear from these results that the perfume intensity was much more intense with Body Wash B (with the capsules of the invention), than with Body Wash I (comparative example). This difference in perfume intensity provides evidence of a better deposition of the capsules comprising guanazole, compared to those comprising guanidine carbonate.

Example 14

Olfactive Evaluation of the Microcapsules of the Invention

Capsules C (according to the invention) as obtained in Example 3 and Capsules J (comparative) as obtained in Example 10 were respectively dispersed in the body wash formulation prepared in Example 12 (Body Wash C and J) so as to achieve a perfume content of 0.2% by weight, relative to the total weight of the body wash formulation (corresponding to 0.67% by weight of the capsules as obtained in Examples 1 and 8, respectively). An amount of 0.5% by weight of an acrylamido-propyl trimonium chloride/acrylamide copolymer (Salcare®, origin: BASF) was also added to the body wash base.

Body Washes C and J were applied to wool swatches intended to mimic human skin, as described in Example 12. The perfume intensity was then evaluated on a blind basis by an expert panel consisting of 4 trained panelists who were asked to rate the perceived perfume intensity on the wool swatches on a scale ranging from 1 to 7, wherein 1 means no odor and 7 means very strong odor, respectively 4 and 8 hours after application of Body Washes C and J. The perfume intensity was evaluated both before and after rubbing the wool swatch with the hand.

Figure 3:
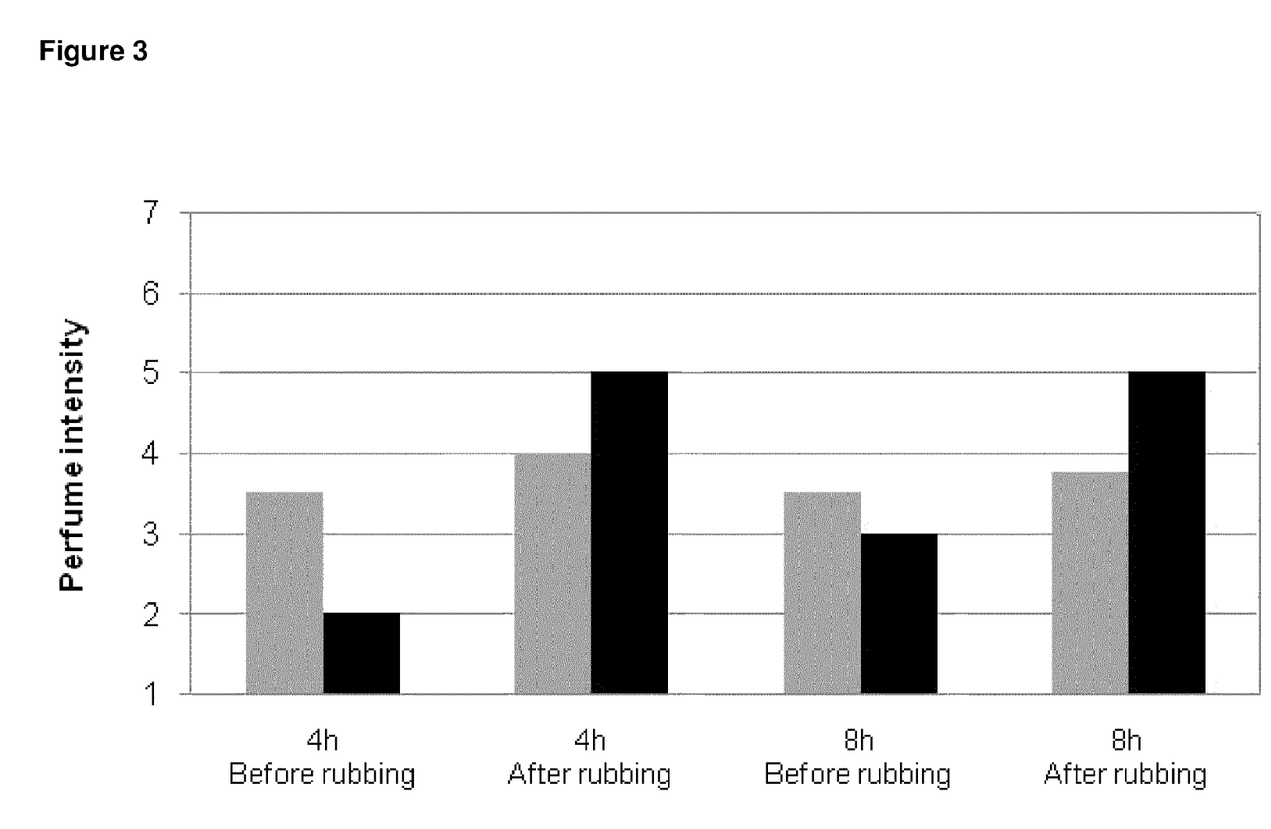
FIG. 3 represents the results of the olfactive evaluation of the capsules of Examples 3 (Capsules C, invention) and 10 (Capsules J, comparative) in body wash application. The perceived perfume intensity of Capsules C is represented in black and that of Capsules J is represented in grey.
Figure 4:
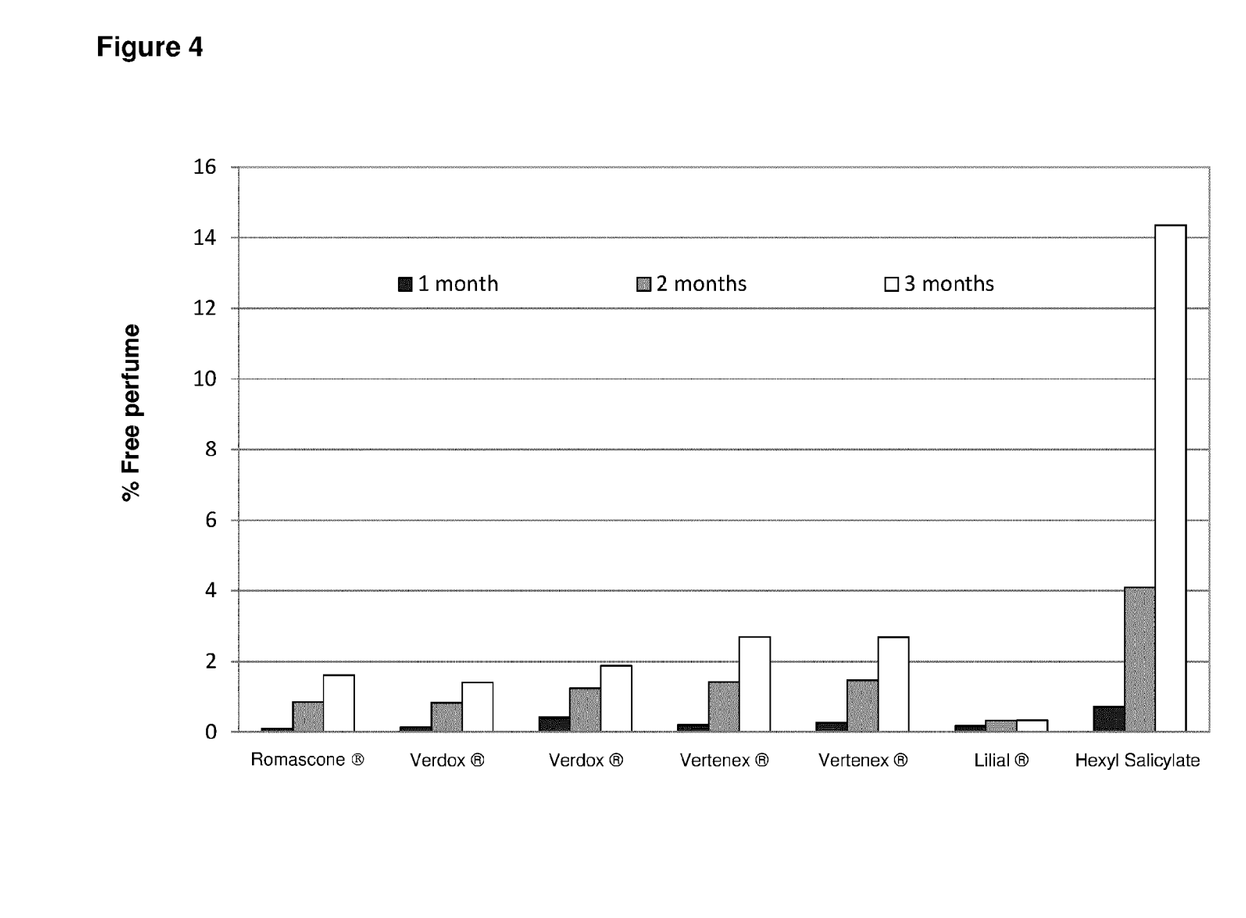
FIG. 4 represents the perfume leakage out of the capsules of Example 1 in body wash formulation at 45° C. It demonstrates the good stability of the capsules in the invention in a body wash consumer product base.

The results are summarized in FIG. 3. It is clear from these results that the perfume intensity was more intense with Body Wash C (with the capsules of the invention) than with Body Wash J (comparative example) after rubbing, both after 4 and 8 hours. This difference in perfume intensity provides evidence of a better deposition of the capsules comprising guanazole, compared to those comprising guanidine carbonate. The perfume intensity being perceived more intensely before rubbing when Body Wash J (comparative) is used is an indication that more perfume leaked out of the capsules. This is confirmed by the fact that the perfume intensity perceived after rubbing is very close to that perceived before rubbing for Body Wash J. In contrast, the difference in perfume intensity before and after rubbing is clear when the swatches are washed with Body Wash C (invention). This therefore provides evidence that the capsules of the invention are better deposited on the wool substrate and also that they better retain the perfume.

The invention claimed is:

1. Polyurea core-shell microcapsules comprising:
   a polyurea shell comprising the reaction product of a polyisocyanate having at least two isocyanate groups with
   i. an amino acid; and
   ii. guanazole; and
   a core comprising a perfume.

2. Polyurea microcapsules according to claim 1, wherein the amino acid is selected form L-lysine and glycine.

3. Polyurea microcapsules according to claim 2, wherein the amino acid is L-lysine.

4. Polyurea microcapsules according to claim 1, wherein the polyisocyanate is an aliphatic polyisocyanate, an aromatic polyisocyanate or a mixture thereof.

5. Polyurea microcapsules according to claim 4, wherein the polyisocyanate is in the form of a mixture of an aliphatic polyisocyanate and an aromatic polyisocyanate in a respective molar ratio ranging from 80:20 to 10:90.

6. Polyurea microcapsules according to claim 1, further comprising an anionic surfactant or stabilizer.

7. A liquid aqueous composition comprising microcapsules as defined in claim 1, together with a cationic polymer.

8. A process for the preparation of polyurea microcapsules comprising:
   a) dissolving at least one polyisocyanate having at least two isocyanate groups in a perfume;
   b) adding an aqueous solution of an amino acid to the mixture obtained in step a) to react with the polyisocyanate; and
   c) adding an aqueous solution of guanazole to the mixture obtained in step b) to react with the reaction product of the polyisocyanate with the amino acid, so as to form a polyurea wall.

9. A process according to claim 8, wherein the amino acid is selected from lysine and glycine.

10. A process according to claim 8, wherein the amino acid is lysine.

11. A perfuming composition or a perfumed consumer product comprising the microcapsules as defined in claim 1 or a liquid composition according to claim 7.

12. A consumer product according to claim 11, in the form of a home- or personal-care product.

13. A consumer product according to claim 11, in the form of a shower gel, a hair care product, an antiperspirant or a deodorant.

14. A consumer product according to claim 12, further comprising a cationic polymer.

15. A consumer product according to claim 14, wherein said cationic polymer is selected from guar hydroxypropyl triammonium polymers, acrylamidopropyl trimonium chloride/acrylamide copolymers and polyquaternium polymers.

* * * * *